(12) United States Patent
Curry

(10) Patent No.: US 10,524,527 B2
(45) Date of Patent: Jan. 7, 2020

(54) ARTICLE OF CLOTHING SUITABLE FOR NURSING OF CHILDREN

(71) Applicant: Alissa Curry, San Antonio, TX (US)

(72) Inventor: Alissa Curry, San Antonio, TX (US)

( * ) Notice: Subject to any disclaimer, the term of this patent is extended or adjusted under 35 U.S.C. 154(b) by 0 days.

(21) Appl. No.: 15/135,537

(22) Filed: Apr. 21, 2016

(65) Prior Publication Data

US 2017/0303606 A1    Oct. 26, 2017

(51) Int. Cl.
*A41F 15/00* (2006.01)
*A41C 3/08* (2006.01)
*A61F 13/14* (2006.01)
*A41D 1/215* (2018.01)
*A41C 3/04* (2006.01)

(52) U.S. Cl.
CPC .............. *A41F 15/002* (2013.01); *A41C 3/04* (2013.01); *A41C 3/08* (2013.01); *A41D 1/215* (2018.01); *A61F 13/141* (2013.01)

(58) Field of Classification Search
CPC ........... A41D 1/205; A41D 1/215; A41C 3/04
USPC ....................................................... 2/104, 109
See application file for complete search history.

(56) References Cited

U.S. PATENT DOCUMENTS

| | | | |
|---|---|---|---|
| 2,585,338 A * | 2/1952 | Meares | A41C 3/04 450/36 |
| 4,528,699 A | 7/1985 | Hughes | |
| 4,660,227 A | 4/1987 | Abramson | |
| 4,663,782 A | 5/1987 | Knox et al. | |
| 4,911,677 A | 3/1990 | White | |
| 6,659,841 B2 * | 12/2003 | Raimondo | A41C 3/04 450/36 |
| 6,854,132 B1 | 2/2005 | Polzin | |
| 6,855,029 B2 * | 2/2005 | Rothman | A41C 3/04 2/104 |
| 7,448,090 B2 | 1/2008 | Lucock | |
| 7,488,234 B2 | 2/2009 | Rothman et al. | |
| 7,878,880 B2 * | 2/2011 | Hendrickson | A41D 1/205 2/104 |
| 7,878,881 B2 | 2/2011 | Hendrickson | |
| 8,226,452 B2 | 7/2012 | Hendrickson | |
| 8,469,770 B2 * | 6/2013 | Alva | A41C 3/04 450/30 |
| 2001/0019933 A1 | 9/2001 | Wagner | |
| 2004/0137821 A1 | 7/2004 | Sandroussi et al. | |
| 2010/0068971 A1 * | 3/2010 | Hendrickson | A41C 3/04 450/31 |
| 2011/0314587 A1 * | 12/2011 | Ritchie | A41C 3/04 2/104 |

(Continued)

*Primary Examiner* — Alissa J Tompkins
*Assistant Examiner* — Brieanna Szafran
(74) *Attorney, Agent, or Firm* — Eric A. Hinojosa

(57) ABSTRACT

The present invention concerns an improved article of clothing for nursing, with features that enhance the user's ability to selectively and controllably expose one or both breasts while simultaneously presenting a more secure and stylish look, both when in use and when not in use. The invention allows for individual or dual breast access in a non-obvious form that can provide as much breast coverage as the mother feels comfortable with. When access to the breast is not in use, the clothing shows no signs of having specific nursing functionality. The invention can be applied to articles of clothing in many fashion design style forms. The invention is also able to optionally provide breast support via an internal brassiere, and nipple protection via removable pads.

8 Claims, 20 Drawing Sheets

(56) References Cited

U.S. PATENT DOCUMENTS

2014/0220860 A1    8/2014  Alva
2014/0273737 A1*  9/2014  Cortese .................... A41C 3/04
                                                          450/31

* cited by examiner

ARTICLE OF CLOTHING SUITABLE FOR NURSING OF CHILDREN

CROSS-REFERENCE TO RELATED APPLICATIONS

This application claims the benefit of provisional patent application No. 62/152,906, submitted and received Apr. 26, 2015.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

Breastfeeding, or nursing, whether in public or private spaces involves a great amount of personal choices. At different times, a nursing mother may desire clothes that focuses on practicality, while at another time style; meanwhile comfort and ease of use are always desired. The present invention describes a novel and heretofore uncontemplated article of clothing for allowing nursing mothers greater freedom in making those important choices. The invention allows for mothers to have it all in one simple and effective package. The invention allows for individual or dual breast access in a non-obvious form that can provide as much breast coverage as the mother feels comfortable with. When access to the breast is not in use, the clothing shows no signs of having specific functionality.

Much of the prior art is essentially a variation on the idea of a removable over layer covering a bottom layer with holes through which the breasts pass. For example see any of the following prior art: CN2094217U, CN2756023Y, CN201709425U, CN204048110U, DE000004324359C2, and U.S. Pat. No. 4,660,227. These designs suffer from significant limitations, not the least of which is the required use of unflattering front pockets which are not suited for many styles of clothing. Another concern is that the pocket flap will not create a good seal of breast coverage, particularly along the side vertical edges. Of course when the user desires access to the breast, the fastening means must be undone. It is well known among nursing mothers that the ability of easy access using one hand is highly desired because the other is typically occupied holding the child or any number of other common items (baby gear, purse, phone, etc.).

Another similar group consists of prior art in which again, there is a bottom layer with holes in it for the breasts to pass through, but that feature one single upper panel of fabric that can be raised to provide access to the breasts. See U.S. Pat. Nos. 8,226,452, 7,878,881, 7,448,090, U.S. patent application Ser. No. 11/625,325, and World Intellectual Property Organization publication number WO2005044028. While some advantage is made in ease of access, problems are again created with security of the clothing when breast access is not desired. Furthermore, controlling exposure and coverage becomes more difficult when breast access is desired.

Another group of prior art features a common theme of providing access to the breast by means of a reversibly detachable fastener holding a breast cup (curved triangular layer) against a bra-like support system that surrounds the breasts. The fastener is typically located at a point above the breast and attached to the support system which is typically a band or string of fabric that runs over the user's shoulder and down the back to engage a lower band that rests around the user's chest and is positioned just under the breasts. See US patent application US20010019933. Due to the mechanisms involved, these are limited to under garments or brassiere and not well suited to many other clothing styles. Additionally, the prior art using this system is notoriously difficult to use; even more so when using one hand.

Yet another group of prior art features relatively simple articles of clothing that feature a vertical or horizontal slit in the panel located over the breast. The slits are sealed with some mechanism such as zippers, buttons, or hook and loop fasteners. See German Patent DE000019800972A1, British Patent GB2246947A, U.S. Pat. Nos. 4,660,227, and 4,663,782 (FIG. 5). These designs are readily identifiable as nursing wear. The obvious and exposed mechanism is often unstylish and undesired by the user as it draws attention. These designs also suffer from reduced ease of access and an increased potential for injury to the breast or nipple. Controlling the amount of exposure or coverage becomes difficult during feeding.

Still another group of prior art discloses the use of individual triangular panels for each breast that can be pulled aside to reveal the breast. See U.S. Pat. No. 4,911,677, World Intellectual Property Organization publication number WO2007053073A1, US patent application US20140220860. In U.S. Pat. No. 6,854,132, an additional over panel covers the triangular panels. The functional elements tend to limit the style of clothing with which the prior art can be used. Again as with other prior art, there is not much control over how much of the breast is exposed for nursing.

It's important to note that coverage may be related to temperature comfort levels, child visibility, child skin contact, a mother's privacy preference, or a mother's modesty preference. Not being able to tightly control the level of exposure may cause the user to forgo wearing the article of clothing altogether in certain environments and social circumstances.

The group of prior art most related to the present invention forgoes the complicated fasteners in favor of a relatively simple system of overlapping layers that are situated to create a horizontal opening at the breasts when the top layer is urged upward and the bottom layer is urged downward. See German Patent DE102004006597A1, European patent application EP1127499A2, and U.S. Pat. No. 4,528,699. The prior art discloses basic articles of clothing that can be made of two separate pieces (featuring a top and bottom section) or one combined piece with two front panels that create the overlap. While these prior art inventions have sought to maximize the ease of access, they fail to provide enough security to prevent unintended access, and leave more to be desired when it comes to controlling the coverage when the user is trying to access their breast. The reason for the lack of security is that they rely on the curvature of the user's breasts and the elasticity of the fabric to create enough friction to stay in place. However, this fails to plan for the eventuality of changing breast size associated with nursing and engorgement periods. These prior arts also fail to plan for the eventuality of changing fabric conditions due to washing, stretching, and shrinking. The reason for the lack of coverage control is similarly a product of not taking into consideration the changing fabric conditions and user measurements.

BRIEF SUMMARY OF THE INVENTION

The present invention will address all of the concerns, failures, and shortcomings of the prior art by describing an improved article of clothing with features that enhance the user's ability to selectively and controllably expose one or both breasts while presenting a more secure and stylish look both when in use and when not in use.

In other words it is a goal of the present invention to provide functionality that can be incorporated into many different styles of clothing.

It is also a goal of the present invention to allow easy access to the breast. The invention allows a user to access the breast with one hand.

It is another goal of the present invention that the user be able to control how much of the breast is exposed during access to the breast and while nursing.

It is yet another goal of the present invention to allow the user to maintain coverage, even while nursing, over any portion of the neck, arms, shoulders, torso, or body that the article would cover while not nursing without drastically distorting the outward appearance of the article of clothing.

It is still another goal of the present invention to be optionally convertible from one style of clothing to another by use of selectively and reversibly detachable features such as sleeves, straps, collars, pads, and internal breast supports.

It is another goal of the present invention to allow the nursing child to have a great deal of visual freedom and improved air flow compared to covers or nursing aprons.

It is a related goal of the present invention to allow the mother-user to have good visual access to the nursing child for improved safety, comfort, and bonding while the child is nursing.

It is another goal that the article maintains the outward appearance of a non-nursing article when not being used for nursing and even when in use for nursing.

It is an important goal of the present invention to offer mothers desiring to nurse an effective, comfortable, and secure article of clothing.

Additional features, goals, and advantages of this invention will be readily understood from the following descriptions, drawings, and claims.

DETAILED DESCRIPTION OF THE INVENTION

The following description is structured to focus on several preferred embodiments. As is commonly understood, the details of these particular descriptions are intended to be illustrative and should not be construed as limitations on the scope of the invention. One of ordinary skill in the art will appreciate that there are many other possible embodiments based on the disclosures made here which are not expressly discussed in detail.

The various embodiments and components may have their position or orientation described by words such as "upwards," "downwards," "vertically," "laterally," "horizontally," "around," "against," etc. These words should be understood in the context of the invention being an article of clothing worn by a person. As such, it will make sense to think of these descriptions in relation to the user (person wearing) the article in a standing position. For example, "upwards," "downwards," and "vertically" would be along the user's standing axis, "horizontally" would be perpendicular to the user's axis, "laterally" would be parallel to the user's axis and located on the user's sides, "around" would be generally defined by the user's body perimeter, and so on.

Figure 1A:
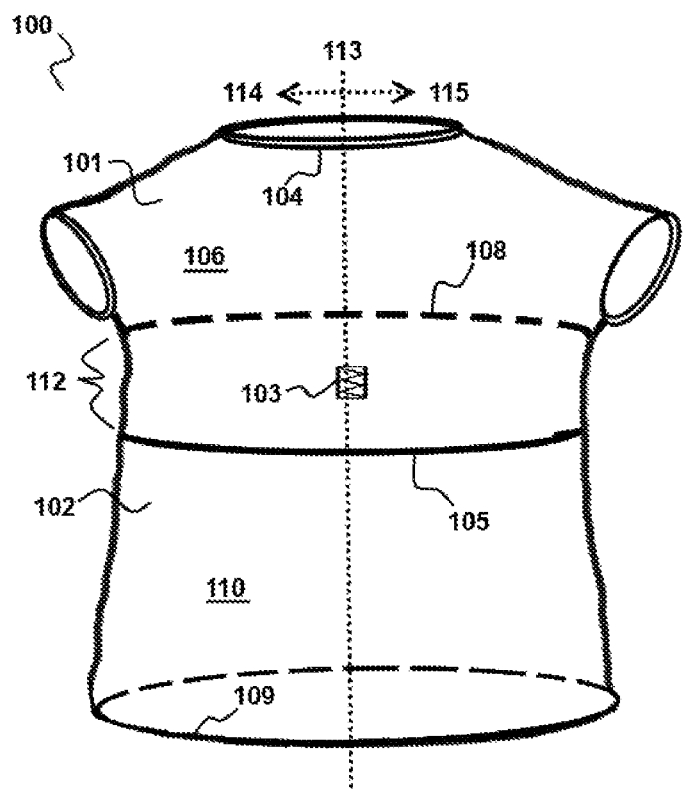
FIG. 1A depicts a simple non reversible connection between the front panels of an article of clothing located in a centered position between the bottom edge of the upper panel and top edge of the lower panel.

For the first embodiment, please refer to FIG. 1A. In a first embodiment, t-shirt 100, the article of clothing is comprised of an upper panel 101, a lower panel 102, and a first connection 103 joining the two. Upper panel 101 is comprised of an upper top edge 104, an upper bottom edge 105, an upper outside face 106, and an upper inside face 107. Lower panel 102 is comprised of a lower top edge 108, a lower bottom edge 109, a lower outside face 110, and a lower inside face 111. Upper panel 101 partially covers lower panel 102 so that upper inside face 107 is pressed against lower outside face 110, and upper bottom edge 105 is positioned lower on a user's torso than lower top edge 108. This creates an overlapping section 112 between upper bottom edge 105 and lower top edge 108. First connection 103 is made in overlapping section 112.

The distance of the overlapping section 112 is comprised by the range between 0.25 inches and 30 inches. In a preferred embodiment, the distance is set so that the upper bottom edge 105 is at least under the curvature of the user's breasts, and so that the lower top edge 108 is at least above the user's nipples. In another embodiment, however, overlapping section 112 is situated so that the center point between upper bottom edge 105 and lower top edge 108 is located above the user's breasts. In yet another embodiment, however, overlapping section 112 is situated so that the center point between upper bottom edge 105 and lower top edge 108 is located below the user's breasts.

Still referring to t-shirt 100, first connection 103 is preferentially positioned along a vertical axis 113 defined by the plane that bisects the user and t-shirt 100 into two opposite but even halves, a right side 114 and a left side 115. In this first embodiment, first connection 103 is further positioned equidistant from upper bottom edge 105 and lower top edge 108. The inclusion of a connection, such as first connection 103 in t-shirt 100, is a novel element that seemingly contradicts the purpose of the article of clothing's overlapping layers. However, by including a point of connection the two breasts are effectively assured of remaining covered until they are accessed. Surprisingly, this does not prevent easy access when the user desires to nurse or use a breast pump. In fact, this connection helps keep the layers aligned to prevent accidental bunch-ups of the upper layer, such as upper panel 101, or accidental roll-downs of the lower layer, such as lower panel 102. When the user is applying force to spread apart the upper and lower layer over one breast, they will feel secure that only that side will be exposed. The connection point also causes the panels to form tighter angles of curvature around the exposed breast section than the prior art since the distance is shortened from the two fixed points of the panel edges along the user's side (as seen in the prior art).

Still referring to t-shirt 100, the lower bottom edge 109 at least partially defines an opening for the user's lower torso. The upper top edge 104 at least partially defines an opening for the user's neck. T-shirt 100 is also comprised by two sleeves attached to two arm holes for the user's arms to pass through on either side.

In another embodiment, upper top edge 104 may at least partially define an opening for the user's upper torso instead of the user's neck (such as for sleeveless article styles). Likewise, in another embodiment, lower bottom edge 109 may at least partially define an opening for the user's legs instead of the user's lower torso (such as for a long dress or skirt article style).

In FIG. 1A, the first connection 103 appears as a square, but that is meant only as an aid to location and is not meant to limit or be representative of the true appearance including shape and dimensions. The connection can be constructed in many different sizes and shapes known in the art.

Figure 1B:
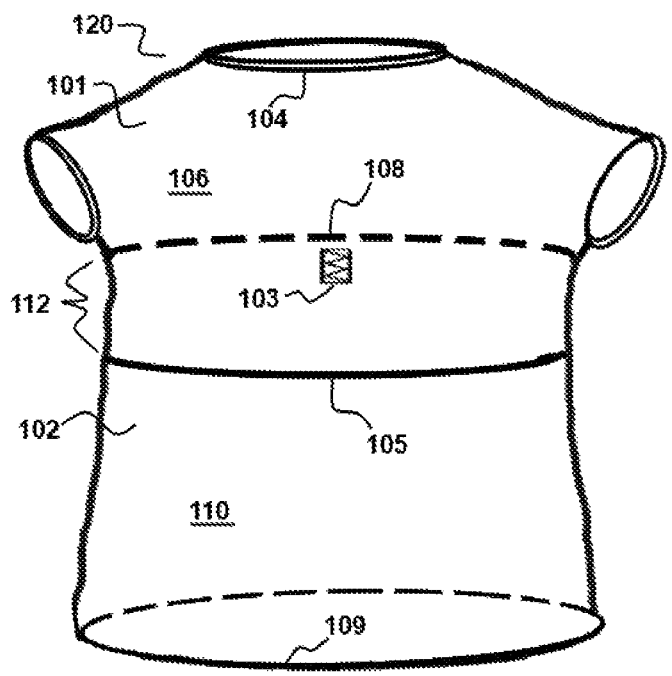
FIG. 1B depicts a simple non reversible connection between the front panels of an article of clothing located in a position relatively closer to the top edge of the lower panel compared to the bottom edge of the upper panel.
Figure 1C:
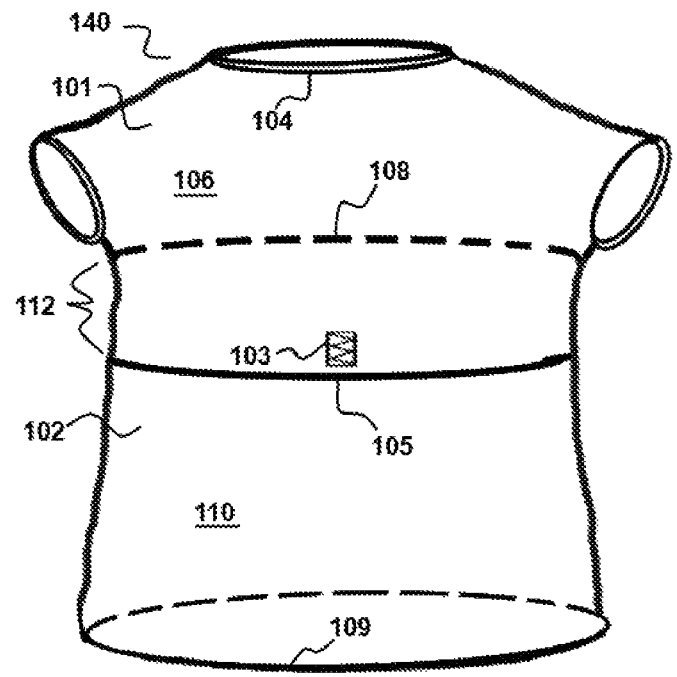
FIG. 1C depicts a simple non reversible connection between the front panels of an article of clothing located in a position relatively closer to the bottom edge of the upper panel compared to the top edge of the lower panel.
Figure 1D:
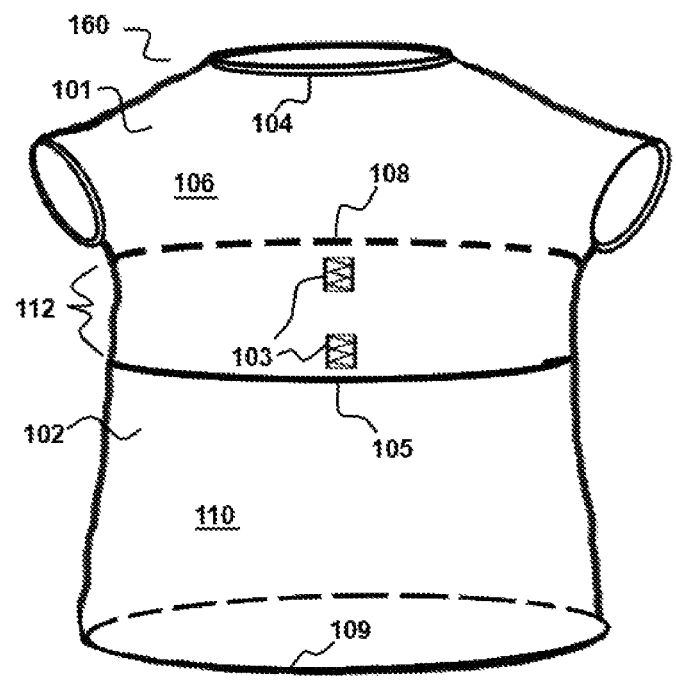
FIG. 1D depicts two simple non reversible connections between the front panels of an article of clothing located along an axis defining the central plane that bisects the article vertically into a right and left half.
Figure 1E:
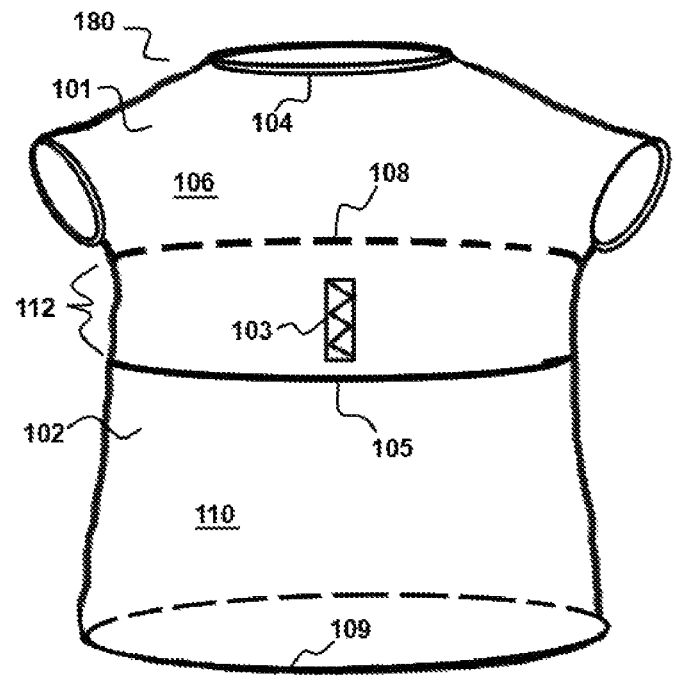
FIG. 1E depicts a simple non reversible connection between the front panels of an article of clothing where the connection is elongated to reach substantially from the top edge of the lower panel to the bottom edge of the upper panel.

In another embodiment similar to t-shirt 100, the first connection 103 is not positioned along the vertical axis 113. In another embodiment, t-shirt 120, first connection 103 is positioned closer to the upper bottom edge 105. See FIG. 1B. In another embodiment, t-shirt 140, first connection 103 is positioned closer to the lower top edge 108. See FIG. 1C. In another embodiment, t-shirt 160 is further comprised of at least a second connection. See FIG. 1D. In another embodiment, t-shirt 180, first connection 103 is elongated to connect more of the distance between upper bottom edge 105 and lower top edge 108. See FIG. 1E. In the above discussed embodiments, the first connection 103 is formed from stitching; however, it could be formed by rivets, adhesives, and other methods of connecting clothing materials well known in the art.

Figure 2A:
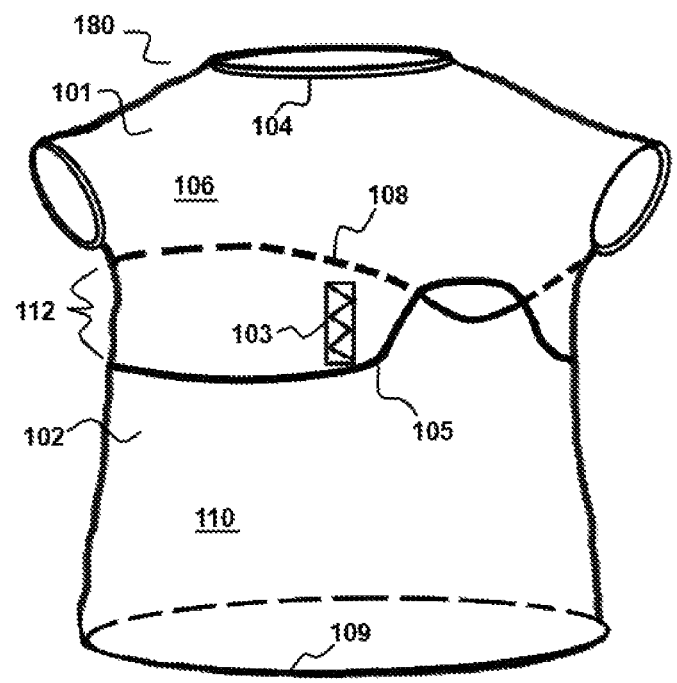
FIG. 2A depicts an article of clothing taking the form of a typical t-shirt with one side of the front panels in the access position.
Figure 2B:
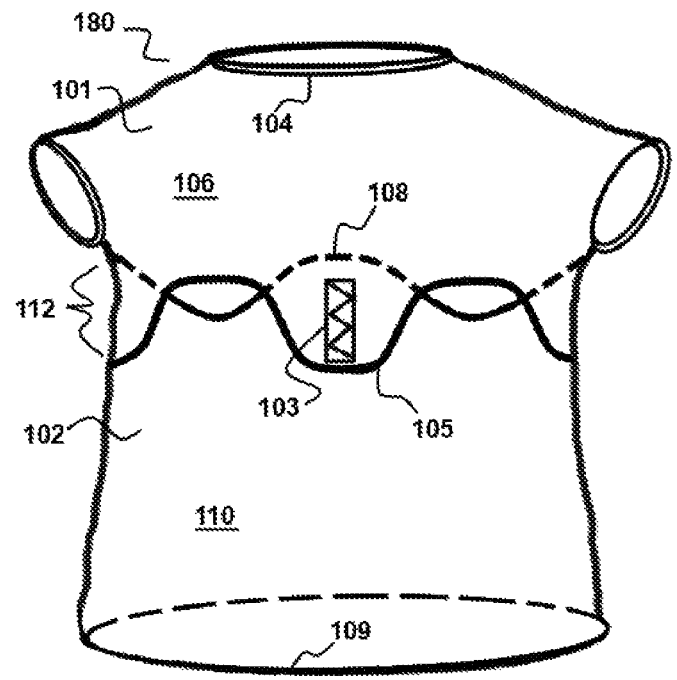
FIG. 2B depicts an article of clothing taking the form of a typical t-shirt with both sides of the front panels in the access position.

In the various embodiments there are at least three well definable positions or states that result from the creation of an overlapping section such as overlapping section 112 in t-shirt 100. The first is the non-access position. This position can be seen in FIG. 1A, FIG. 1B, FIG. 1C, FIG. 1D, and FIG. 1E. There is a second position, the single access position, whereby the user creates an opening in the article of clothing by urging the upper panel and lower panel apart at the overlapping section on either side of the connection; for example when a user urges apart upper panel 101 and lower panel 102 at right side 114 or left side 115 of overlapping section 112, of t-shirt 100. See FIG. 2A. The third position, the double access position, is when the user creates two openings by repeating the maneuver described above for both right side 114 and left side 115. See FIG. 2B.

Figure 3A:
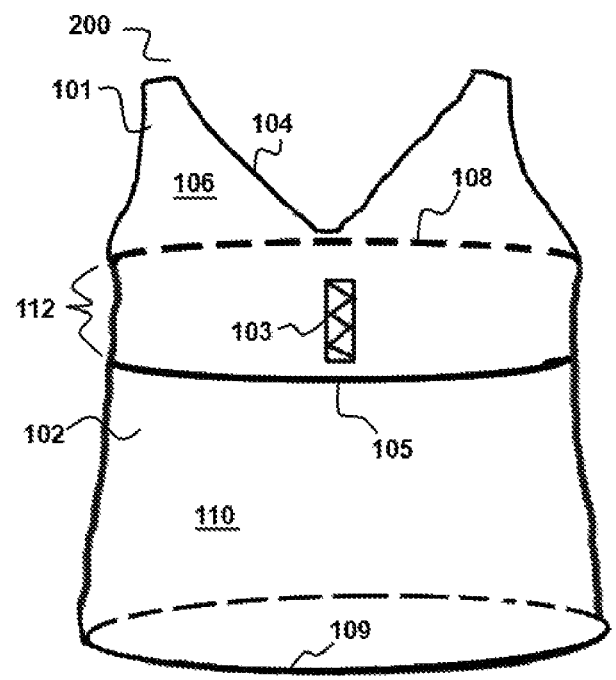
FIG. 3A depicts an article of clothing taking the form of a typical sleeveless shirt with both sides of the front panels in the non-access position.
Figure 3B:
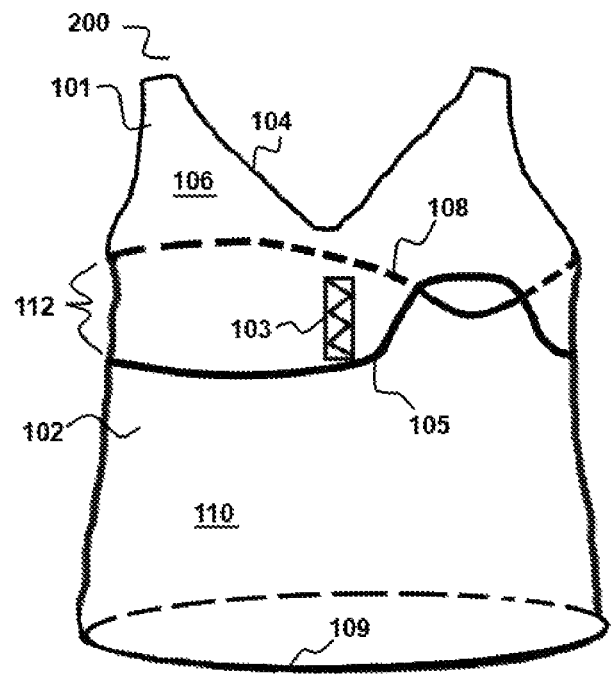
FIG. 3B depicts an article of clothing taking the form of a typical sleeveless shirt with one side of the front panels in the access position.
Figure 3C:
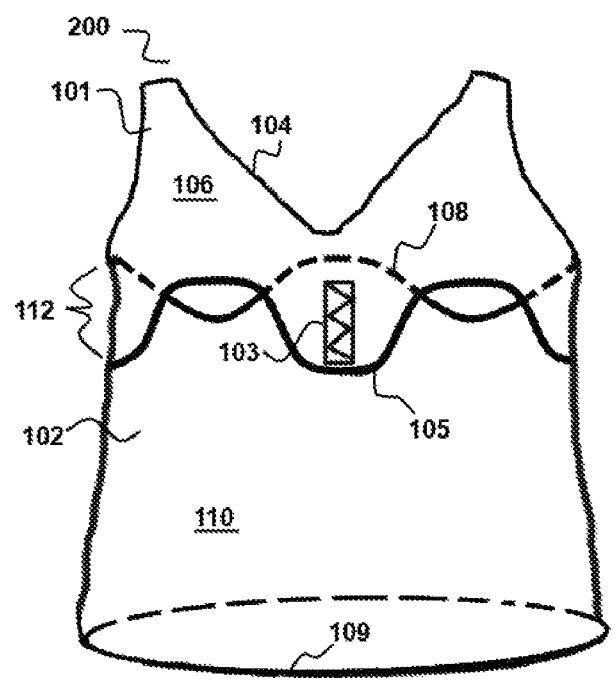
FIG. 3C depicts an article of clothing taking the form of a typical sleeveless shirt with both sides of the front panels in the access position.
Figure 4A:
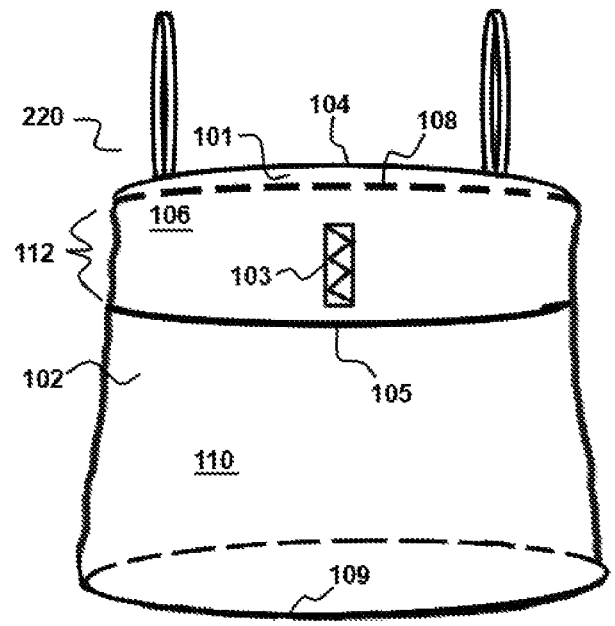
FIG. 4A depicts an article of clothing taking the form of a typical spaghetti top with both sides of the front panels in the non-access position.
Figure 4B:
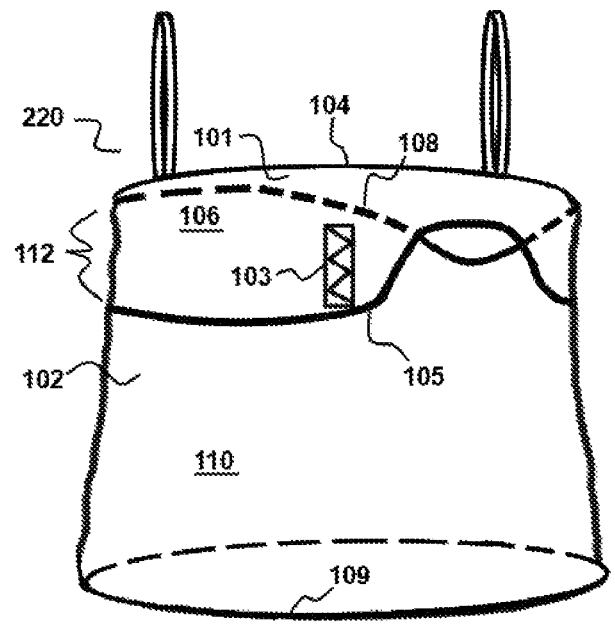
FIG. 4B depicts an article of clothing taking the form of a typical spaghetti top with one side of the front panels in the access position.
Figure 4C:
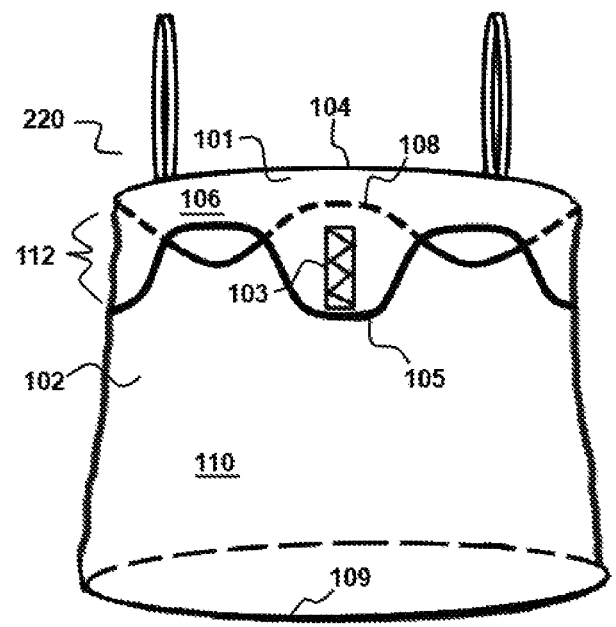
FIG. 4C depicts an article of clothing taking the form of a typical spaghetti top with both sides of the front panels in the access position.

In another embodiment, sleeveless shirt 200, the article of clothing features a sleeveless shirt style form, rather than a t-shirt style form. See FIG. 3A. In another embodiment, spaghetti strap top 220, the article of clothing features a spaghetti strap top style form. See FIG. 4A. Though the style form can readily be changed, there is no loss of function with respect to allowing the user to go from non-access to access positions as desired. See FIG. 3B, FIG. 3C, FIG. 4B, and FIG. 4C. Those of ordinary skill in the art will appreciate that many other style forms could be substituted for the examples of the t-shirt, sleeveless shirt, and spaghetti strap top used above. For example, the invention could be practiced on a tube top, a dress, a gown, a brassiere, lingerie, a skirt, a sweater, a long sleeve shirt, a hoodie, a coat, hospital gown, a tank top, a sports bra, a bandeau, a bathing suit, pajamas, etc. This applies to all of the embodiments and features described throughout this invention.

Figure 5A:
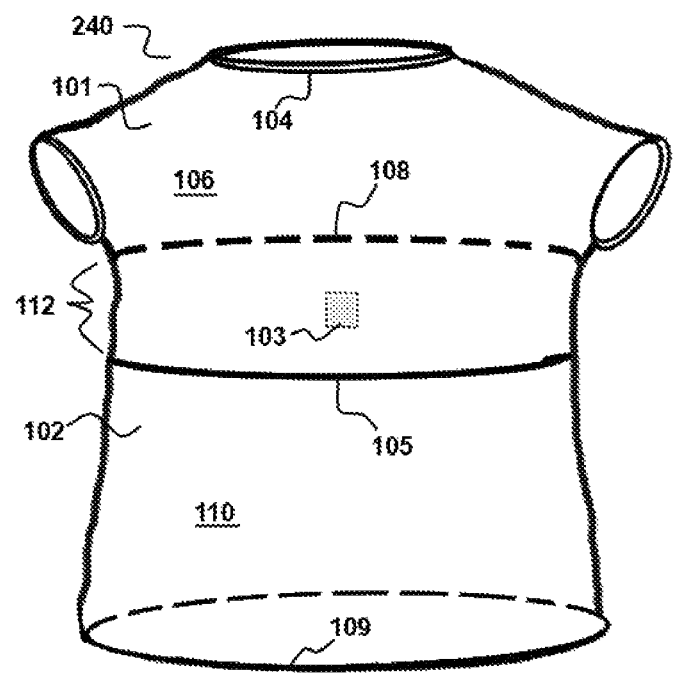
FIG. 5A depicts a simple reversibly detachable connection between the front panels of an article of clothing located in a centered position between the bottom edge of the upper panel and top edge of the lower panel, where the connection is attached and the panels are in the non-access position.

In another embodiment, t-shirt 240, the first connection 103 is a reversibly detachable connection that can be optionally attached or detached by the user. In this embodiment, first connection 103 is made of hook and loop (Velcro®) strips. See FIG. 5A. Hook and loop is a desirable material of construction because it has the advantage of not being visible on the surface of the article of clothing such as upper outside face 106 on t-shirt 100. This feature is a desirable attribute, but not required. Any number of other suitable replacements commonly known in the industry could be substituted for hook and loop so long as the result is a reversibly detachable connection. For example, button snaps, button and buttonhole, magnets, hook and eye, clasps, d-rings, string-ties, etc. could easily take the place of the hook and loop in this and the other embodiments.

Figure 5B:
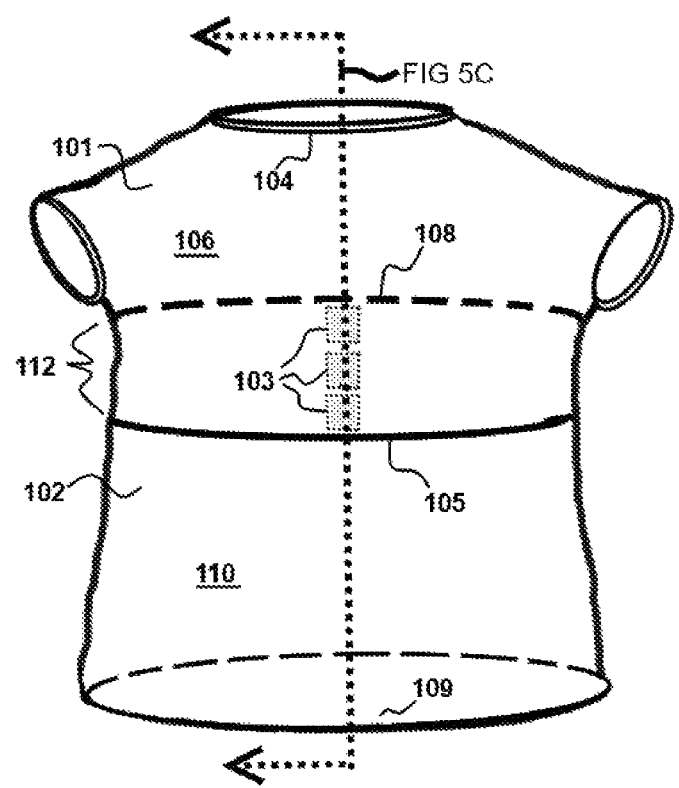
FIG. 5B depicts three optional positions for a simple reversibly detachable connection between the front panels of an article of clothing located along an axis defining the central plane that bisects the article vertically into a right and left half.
Figure 5C:
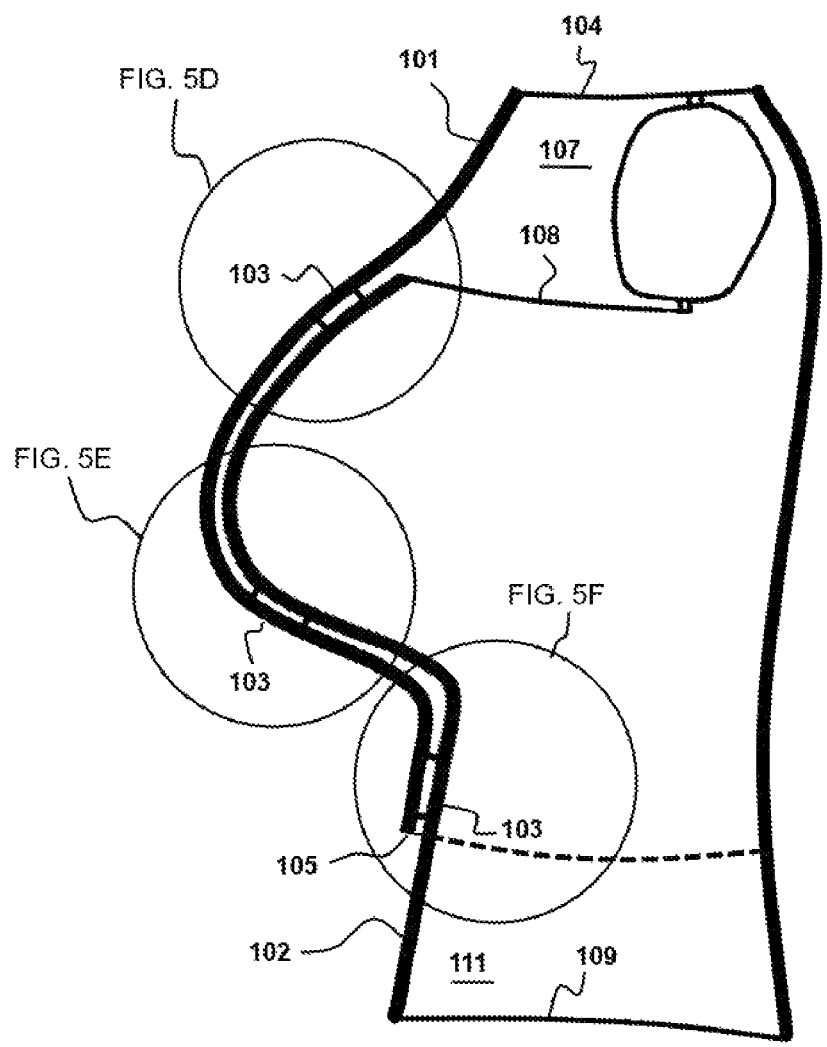
FIG. 5C is a sectioned isometric view, or cutaway view, of the interior of an article of clothing depicting three optional positions for a simple reversibly detachable connection between the front panels of the article of clothing.
Figure 5D:
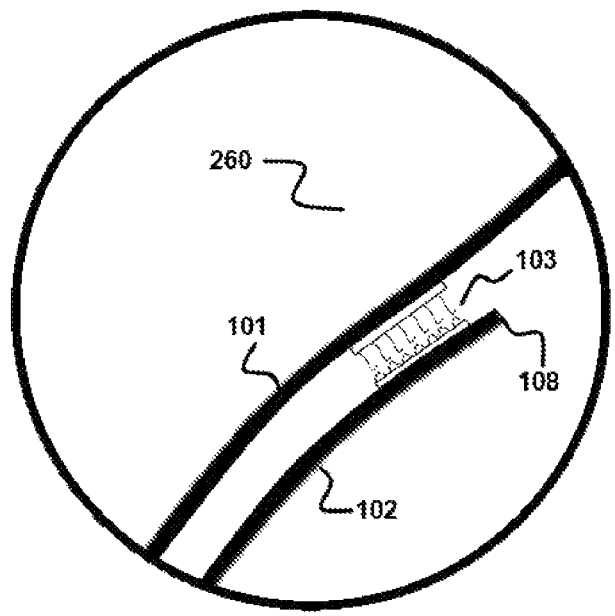
FIG. 5D is a magnified view of a first reversibly detachable connection between the front panels of the article of clothing, where the connection is positioned relatively closer to the top edge of the lower panel compared to the bottom edge of the upper panel.
Figure 5E:
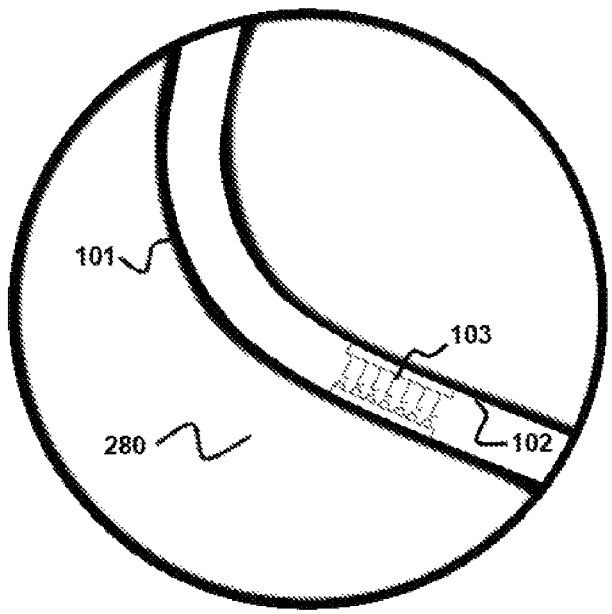
FIG. 5E is a magnified view of a second reversibly detachable connection between the front panels of the article of clothing, where the connection is positioned relatively centered between the top edge of the lower panel and the bottom edge of the upper panel.
Figure 5F:
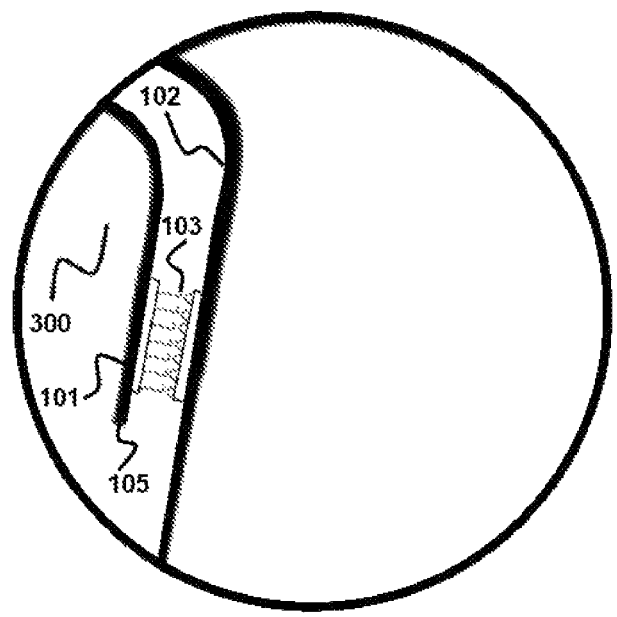
FIG. 5F is a magnified view of a third reversibly detachable connection between the front panels of the article of clothing, where the connection is positioned relatively closer to the bottom edge of the upper panel compared to the top edge of the lower panel.

In the same embodiment, t-shirt 240 there is a multiplicity of positions where the reversibly detachable connection 103 could be located with respect to upper bottom edge 105 and lower top edge 108. See FIG. 5B. Each position represents another variation of the embodiment, and hence its own embodiment. The positions of the reversibly detachable connections are best seen in FIG. 5C and magnifications FIG. 5D, FIG. 5E, and FIG. 5F. First connection 103 is located at each of these positions in separate but related embodiments. Referring to FIG. 5D, t-shirt 260 has first connection 103 positioned closer to lower top edge 108. Referring to FIG. 5E, t-shirt 280 has first connection 103 positioned closer to the center point located between upper bottom edge 105 and lower top edge 108. Referring to FIG. 5F, t-shirt 300 has first connection 103 positioned closer to upper bottom edge 105. Each position has advantages and disadvantages for ease of use, ability to control the opening in an access position, and security of article of clothing in the non-access position. The optimal selection will depend on factors such as style of the article, size and shape of the user, and user's preference.

In another embodiment there is at least a second connection. The first connection and the at least a second connection are located collinearly in a further related embodiment.

Figure 5G:
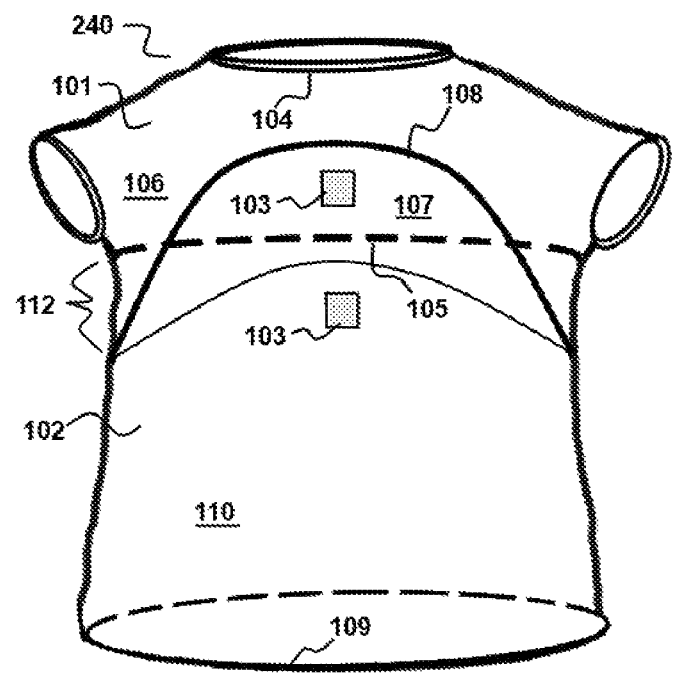
FIG. 5G depicts a simple reversibly detachable connection between the front panels of an article of clothing located in a centered position between the bottom edge of the upper panel and top edge of the lower panel, where the connection is detached and the upper panel is pulled up.

Earlier, in an above paragraph, three definable positions were described—non-access, single access, and double access—defining a particular state the article of clothing could be manipulated into by the user. However, the use of a reversibly detachable connection allows for a fourth position, the dual access position. In the dual access position, the user can detach the connection between the upper and lower panels to create a larger opening in the overlapping section. This allows access to both the right side 114 and the left side 115 through the larger opening. See FIG. 5G.

With respect to FIG. 6A, FIG. 6B, FIG. 6C, FIG. 7A, FIG. 7B, FIG. 8A, and FIG. 8B, each is a sectioned isometric view, or cutaway view of the interior of the article of clothing in a particular embodiment. Each of the referenced figures shows the front side of the article on the left, the back side on the right, an arm-hole on the upper right side, a neck hole along the top edge and an opening for the torso along the bottom edge.

So far the descriptions have focused on the functional components and features of particular embodiments and related embodiments. The manner in which the components come together to form the functional garment has largely been ignored with the exception of certain novel features. This is because there are an infinite number of ways in which the sides, back, neck, arms, straps, or torso-hole could be formed without affecting the access and non-access functionality created by the novel features of this invention. However, in FIG. 6A, FIG. 6B, and FIG. 6C these fabrication concerns are addressed. The mentioned figures disclose particular seam patterns, where each seam pattern represents another embodiment that could be used in combination with any of the other embodiments discussed in the other paragraphs.

Figure 6A:
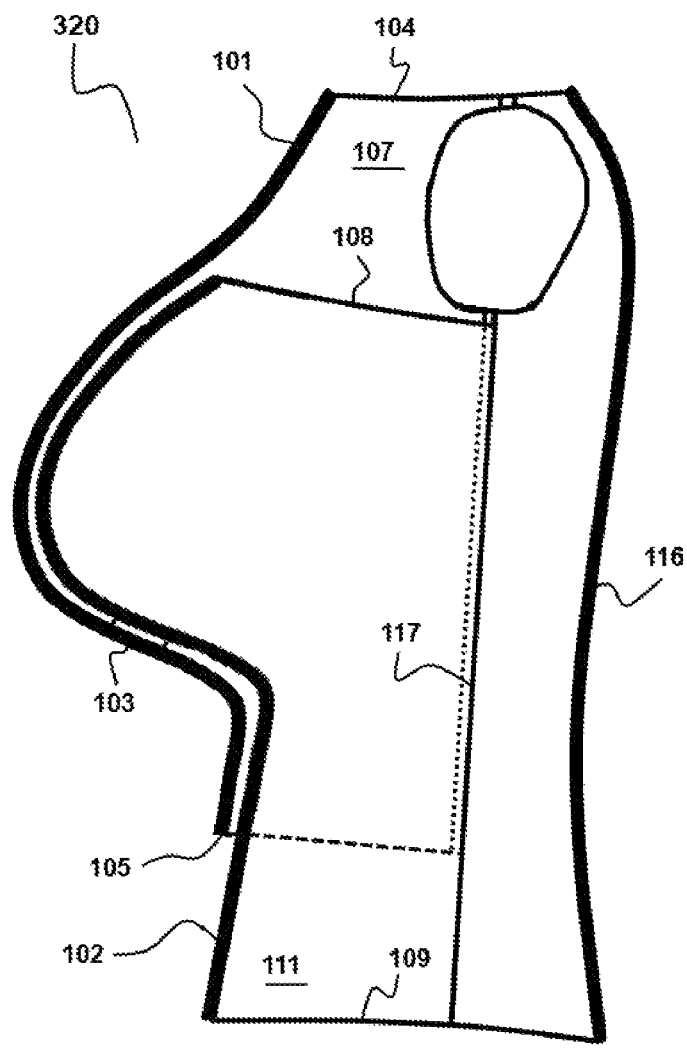
FIG. 6A depicts a first pattern of seams where the front panels join the back panel along a vertical seam running from the base of the article of clothing and up along the side to the neck of the article of clothing.

In FIG. 6A, t-shirt 320 is further comprised by a back panel 116 and a lateral seam 117, where lateral seam 117 connects the upper panel 101 to the lower panel 102 and the back panel 116. The lateral seam 117 runs laterally from the lower bottom edge 109 up to the lower top edge 108. The lateral seam 117 continues just under the arm hole, around the arm hole to attach sleeves if any are present, and just above it over the user's shoulders to the neck hole formed by upper top edge 104. In a related, but not depicted, embodiment that features the sleeveless style form, lateral seam 117 joins only the upper panel 101 to back panel 116.

Figure 6B:
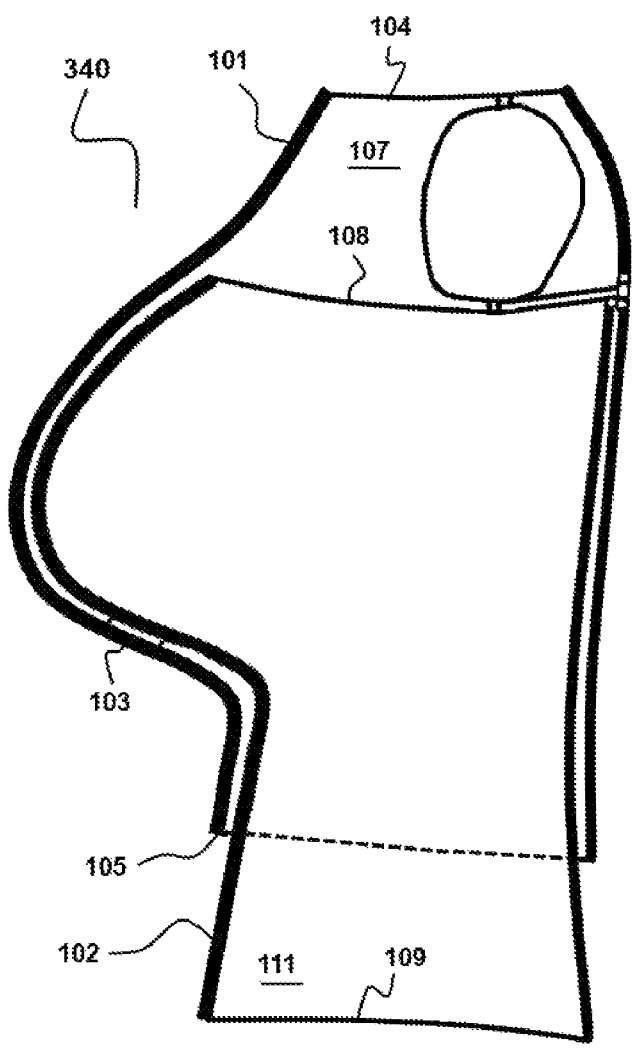
FIG. 6B depicts a second pattern of seams where the upper front panel joins an upper back panel along a vertical seam running from the neck of the article of clothing down to the top edge of the lower panel. In this pattern the lower panel may be formed from a single tubular produced material or a vertical seam may be used. A horizontal seam joins the bottom edge of the upper back panel to a portion of the back of the top edge of the lower panel.

In another embodiment, t-shirt 340 seen in FIG. 6B, has upper panel 101 and lower panel 102 fabricated from tubular fabric so that no seam is necessary except for the sleeves, if any, and likewise no back panel is necessary. In another embodiment, not shown in the figures, a tack seam 118 is added along the back or sides of the article to join upper panel 101 and lower panel 102.

Figure 6C:
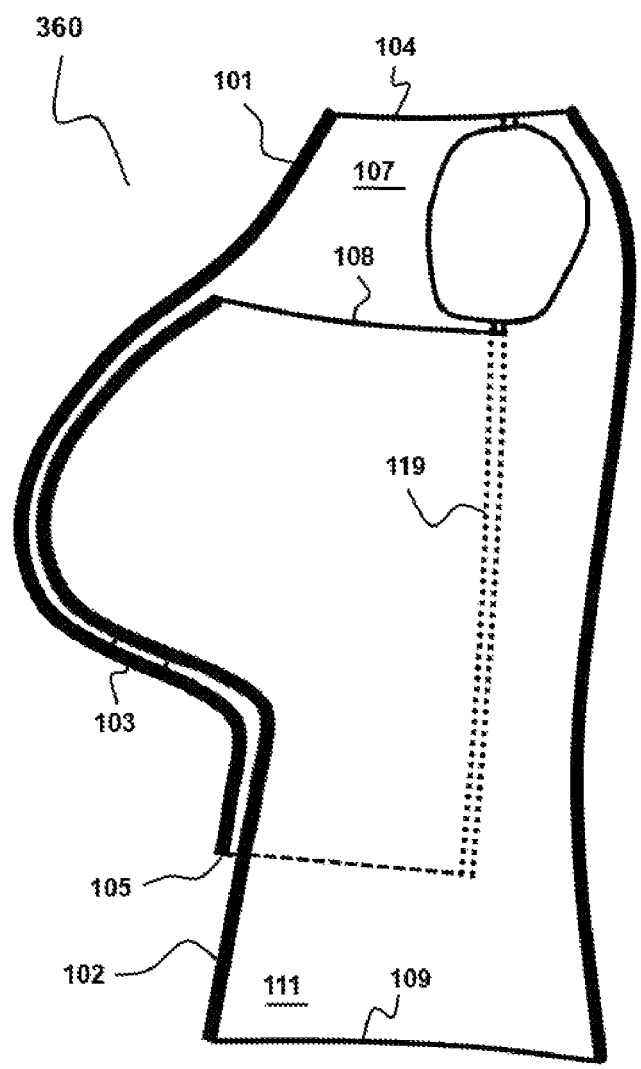
FIG. 6C depicts a third pattern of seams where the lower panel may be formed from a single tubular produced material, or a vertical seam may be used, but the upper panel is joined to the lower panel along vertical seams positioned along the side and extending from the bottom edge of the upper panel to the top edge of the lower panel.

In another embodiment, t-shirt 360 seen in FIG. 6C, has a hybrid of the seam patterns seen in FIG. 6A and FIG. 6B. In t-shirt 360 the lower panel 102 is fabricated of tubular material, but the upper panel 101 is not, resulting in a partial lateral seam 119 that joins the upper panel 101 to the lower panel 102 from the upper bottom edge 105 up to the lower top edge 108, which continues on the user's shoulders to the neck hole formed by upper top edge 104. The partial lateral seam 119 also joins the sleeves if any are present at the arm hole.

Figure 7A:
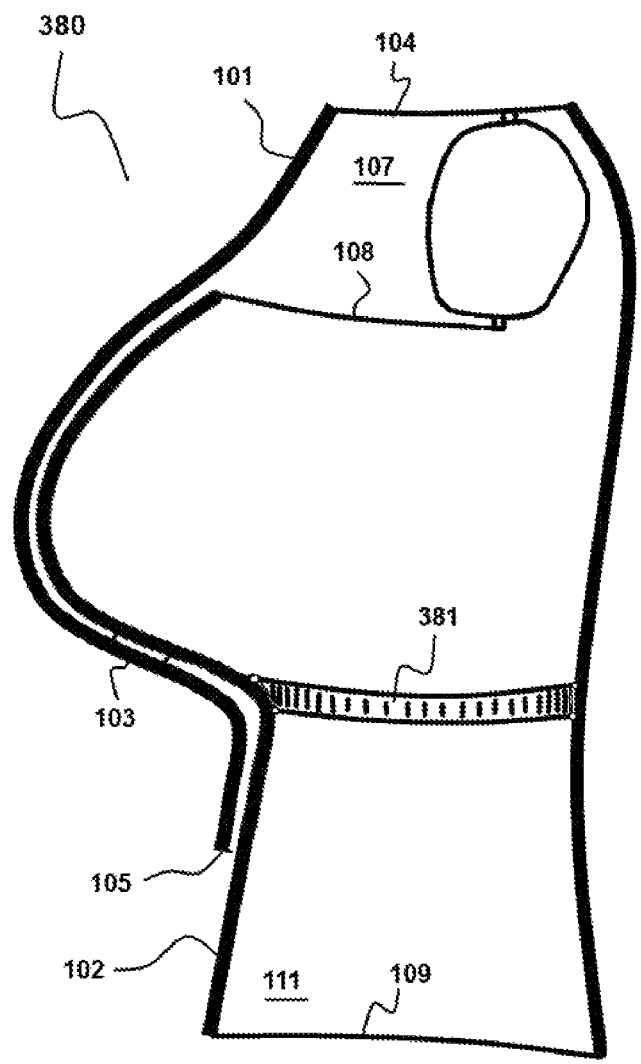
FIG. 7A depicts an article of clothing featuring an upper panel, a lower panel, at least one connection between the two panels, and an internal support band positioned to rest snugly against and around the user's chest just below their breasts.

Another embodiment seen in FIG. 7A, t-shirt 380 is similar to t-shirt 100 but is further comprised of an internal elastic band 381. The internal elastic band 381 is positioned along the lower inside face 111, so that it rests snugly against the user's torso at a position just under the user's breasts. The internal elastic band 381 gives support to the breasts and helps to secure the position of the lower panel 102.

Figure 7B:
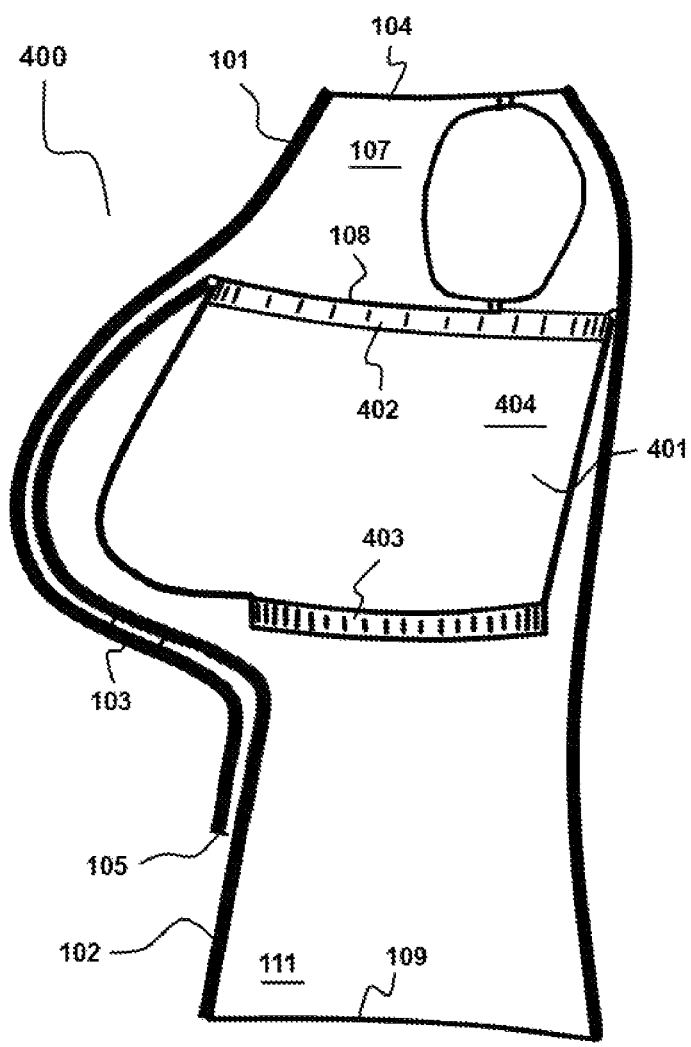
FIG. 7B depicts an article of clothing featuring an upper panel, a lower panel, at least one connection between the two panels, and an internal brassiere comprised of a lower support band, an upper support band, and a tubular layer of fabric material that connects the two. The upper support band is connected to the top edge of the lower panel, but the lower support band is not connected directly to the lower panel.

Yet another embodiment seen in FIG. 7B, t-shirt 400, is similar to t-shirt 100 but is further comprised of an internal brassiere support system, bra 401. The bra 401 is comprised of an upper elastic band 402, a lower elastic band 403, and a tubular layer of fabric, bra body 404, connecting the two elastic bands (402 and 403). The lower elastic band 403 hangs freely from bra body 404 and is otherwise unconnected to the rest of t-shirt 400, while the upper elastic band 402 is connected to t-shirt 400 at the lower top edge 108. In a similar embodiment, the connection between upper elastic band 402 and lower top edge 108 is reversibly detachable. By virtue of being reversibly detachable, the user can optionally connect the bra 401 when desired or disconnect it when not desired.

Figure 8A:
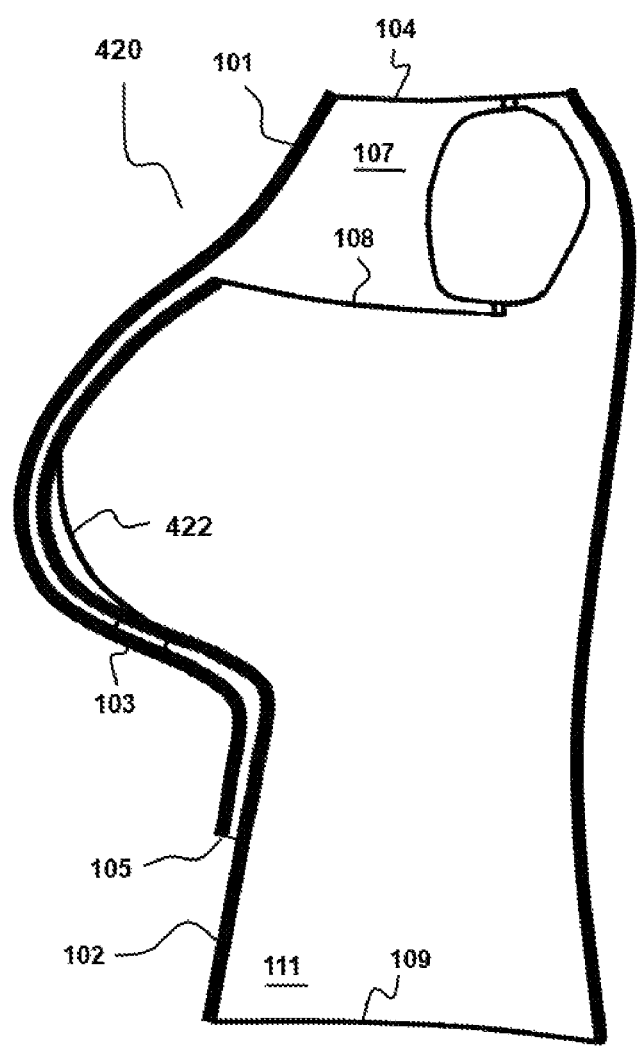
FIG. 8A depicts an article of clothing featuring an upper panel, a lower panel, at least one connection between the two panels, and an internal nipple pad positioned on the interior of the lower panel.

Still another embodiment seen in FIG. 8A, t-shirt 420, is similar to t-shirt 100 but is further comprised of left nipple pad 421 and right nipple pad 422. Left and right nipple pad 421 and 422 are each positioned to rest between the user's left and right nipple, respectively and the lower inside face 111. In a similar embodiment, the left nipple pad 421 and right nipple pad 422 are reversibly connectable to lower inside face 111, and can be positionally adjusted by the user to optimize placement for the user's individual dimensions. It is understood that left nipple pad 421 and right nipple pad 422 can be constructed of disposable or non-disposable, washable, and reusable materials.

Figure 8B:
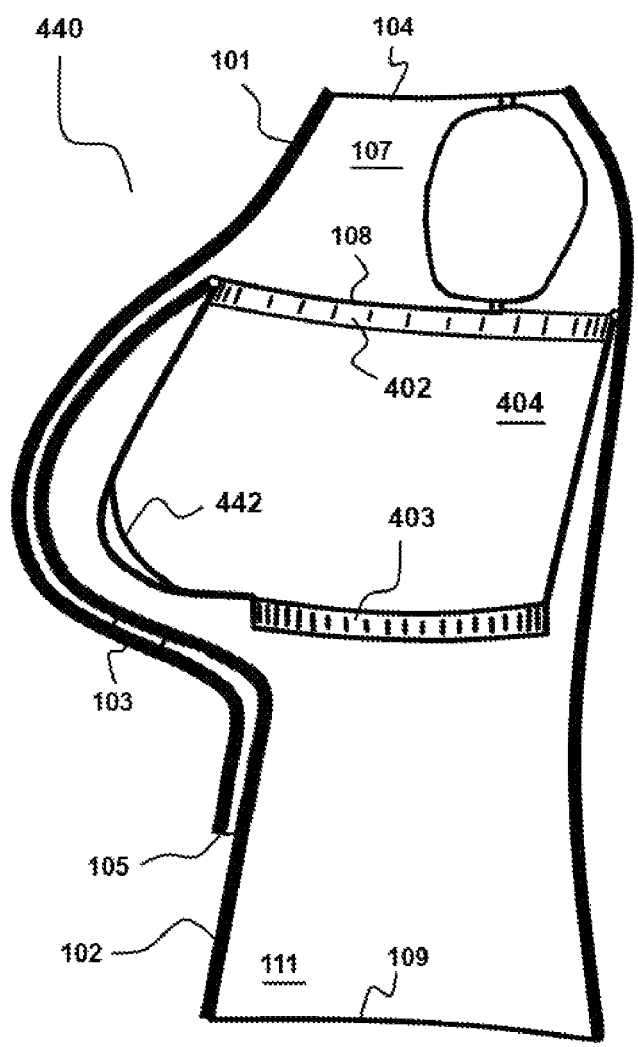
FIG. 8B depicts an article of clothing featuring an upper panel, a lower panel, at least one connection between the two panels, an internal brassiere comprised of a lower support band, an upper support band, a tubular layer of fabric material that connects the two, and an internal nipple pad positioned on the interior of the tubular layer of fabric material.

A combination embodiment seen in FIG. 8B, t-shirt 440, is similar to t-shirt 400, but the brassiere support system, bra 401 is further comprised of bra left nipple pad 441 and bra right nipple pad 442. Bra left nipple pad 441 and bra right nipple pad 442 are each positioned, respectively, to rest between the user's left and right nipple and the bra body 404.

In a similar embodiment, the bra left nipple pad 441 and bra right nipple pad 442 are reversibly connectable to bra body 404, and can be positionally adjusted by the user to optimize placement for the user's individual dimensions. It is understood that bra left nipple pad 441 and right nipple pad 442 can be constructed of disposable or non-disposable, washable, and reusable materials.

In another embodiment, not pictured, the use of style or design features are used to further conceal the existence and function of the upper and lower panels. For example, in one embodiment, pleats are used to disguise the seams. In another example embodiment, particular patterns and colors are used to disguise the seams and the edges of the overlapping section 112. In another example embodiment, the use of bands, accomplishes the same. In another, the use of belts accomplishes the same.

Figure 9A:
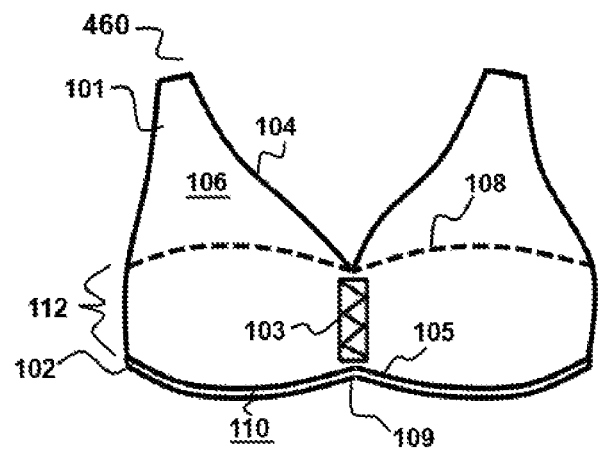
FIG. 9A depicts an article of clothing in the style of a swimsuit top comprised of an upper panel, a lower panel, and at least one connection between the two panels.

Another embodiment, swimsuit 460, seen in FIG. 9A, is an article of clothing in the style of a swimsuit top and is comprised of an upper panel 101, a lower panel 102, and at least one connection 103 between the two panels.

Figure 9B:
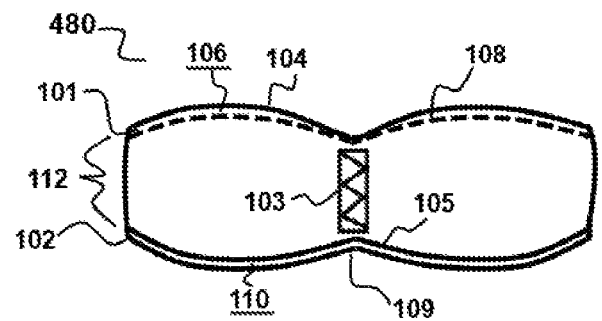
FIG. 9B depicts an article of clothing in the style of a bandeau comprised of an upper panel, a lower panel, and at least one connection between the two panels.

In another embodiment, bandeau 480, seen in FIG. 9B, the article of clothing is in the style of a bandeau and is comprised of an upper panel 101, a lower panel 102, and at least one connection 103 between the two panels.

Figure 10A:
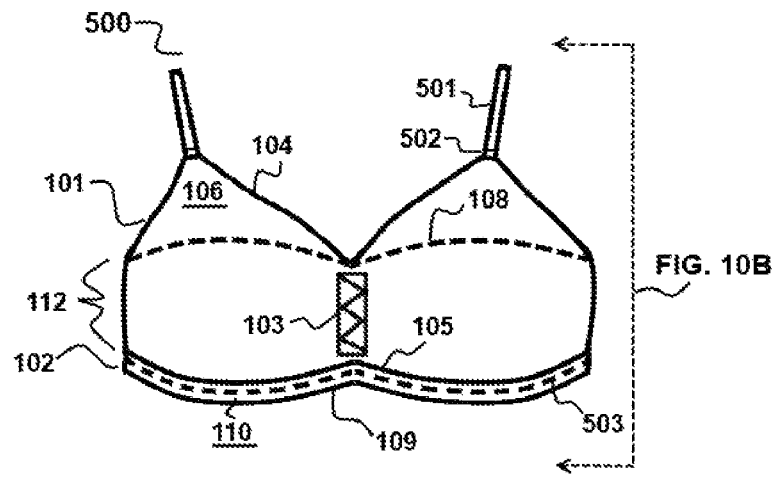
FIG. 10A depicts an article of clothing in the style of a brassiere comprised of an upper panel, a lower panel, at least one connection between the two panels, at least one reversibly detachable shoulder strap connected to the upper panel, and a reversibly detachable breast support member connected to the lower panel.
Figure 10B:
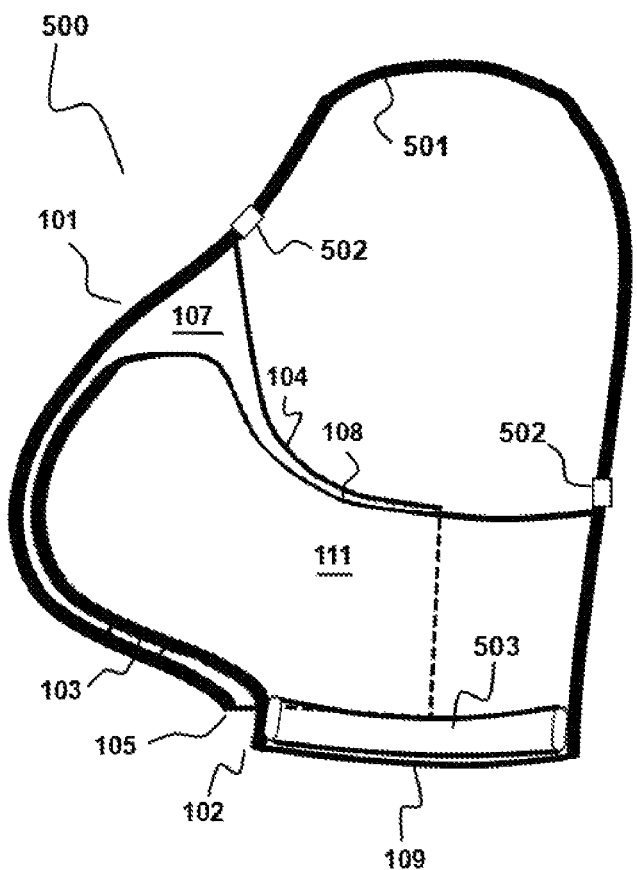
FIG. 10B is a sectional depiction of the article of clothing of FIG. 10A showing the inside of the article of clothing in more detail.

FIG. 10A depicts another embodiment, brassiere 500, which is an article of clothing in the style of a brassiere comprised of an upper panel 101, a lower panel 102, at least one connection 103 between the two panels, at least one reversibly detachable shoulder strap 501 connected to the upper panel by at least one connector 502, and a reversibly detachable breast support member 503 connected to the lower panel. See FIG. 10B for an additional view of brassiere 500 showing the inside of the article of clothing in more detail. It is well known in the art that breast support member 503 can be made of a resilient but flexible material such as metal, fiberglass, resin, and plastics.

Even though the above embodiments discussed a single overlapping section 112, it is understood that multiple overlapping sections could be created in the same article of clothing. It will also be readily understood by those of ordinary skill in the art that an article of clothing having multiple overlapping sections could have those sections stacked and aligned upon one another. Take for example another embodiment similar to t-shirt 400, called sport-shirt 520 (not shown in the drawings) comprised of the first overlapping section 112, and further comprised of a second overlapping section 524 built into the bra 401 by replacing bra body 404 with upper bra panel 521, lower bra panel 522, and bra connection 523. In sport-shirt 520, the upper bra panel 521 has a top edge that is connected to the upper elastic band 402, and the lower bra panel 522 has a bottom edge is connected to the lower elastic band 403. Furthermore, upper bra panel 521 has a bottom edge that is positioned below a top edge of lower bra panel 522. The lower bra panel 522 is also positioned between the user and upper bra panel 523, creating the second overlapping section 524. The bra connection 523 connects lower bra panel 522 to upper bra panel 521 in the overlapping section 524.

Although the invention has been described and illustrated with a certain degree of detail or with reference to one or more particular embodiments, it is understood that the present disclosure has been made only by way of example. It should be understood that the invention is not intended to be limited to the particular forms disclosed. Furthermore, the invention is amenable to various modifications and alternative forms. Obvious variations and other various changes in the composition, combination, and arrangement of parts can be utilized to by those skilled in the art without departing from the spirit and scope of the invention, as herein disclosed and claimed.

What is claimed is:

1. An article of clothing, to be worn by a user on a torso of the user, comprising:
   an upper panel, having a first area defined by a bottom edge of said upper panel, a right side edge of said upper panel, a left side edge of said upper panel, and a top edge of said upper panel, wherein the upper panel is configured to extend across a chest of the user when the article is worn by the user, and further wherein the bottom edge of the upper panel is configured to be positioned below breasts of the user when the article is worn by the user;
   a lower panel, having a second area defined by a bottom edge of said lower panel, a right side edge of said lower panel, a left side edge of said lower panel, and a top edge of said lower panel, wherein the lower panel is configured to extend across the user's chest when the article is worn by the user, and further wherein the top edge of said lower panel is configured to be positioned above nipples of the user when the article is worn by the user;
   a back panel, wherein the back panel is connected to the right and left side edges of the upper panel and the right and left side edges of the lower panel, and further wherein the back panel is configured to extend across a back of the user when the article is worn by the user;
   an overlapping area created by said first area of the upper panel and said second area of the lower panel, where said lower panel is positioned at least partially beneath said upper panel, and further where said lower panel is configured to be placed next to the user's chest;
   at least one center connection, joining said upper panel to said lower panel, wherein the at least one center connection is configured to be located in said overlapping area, and along an axis defined by a vertical plane of symmetry that divides the article into a left and a right side;
   a right side breast access is formed in the overlapping area, configured to be positioned below a right breast of the user's breasts when the article is worn, wherein the right side breast access is defined by the bottom edge of the upper panel, the top edge of the lower panel, the right side edge of the upper panel, the right side edge of the lower panel, and the at least one center connection;
   a left side breast access is formed in the overlapping area, configured to be positioned below a left breast of the user's breasts when the article is worn, wherein the left side breast access is defined by the bottom edge of the upper panel, the top edge of the lower panel, the left side edge of the upper panel, the left side edge of the lower panel, and the at least one center connection;
   wherein the upper panel and the lower panel are comprised of a material that is resiliently deformable;
   further wherein the right side breast access and the left side breast access each have a non-access state wherein the bottom edge of the upper panel is lower than the top edge of the lower panel, and a single access state wherein the bottom edge of the upper panel is higher than the top edge of the lower panel; and
   an internal brassiere, comprised of a tubular bra body connecting an upper elastic band to a lower elastic band, positioned within the article of clothing such that the upper elastic band is reversibly connected to the top edge of the lower panel wherein the internal brassiere is configured to be placed next to the user's chest.

2. The article of clothing of claim 1 further comprising:
   at least one nipple pad, positioned beneath the internal brassiere, wherein said at least one nipple pad is absorbent and is configured to be placed against a nipple of the user's nipples.

3. The article of clothing of claim 1 wherein the at least one center connection is selected from a first group of irreversible fasteners comprising:
   stitching, rivets, and adhesives.

4. The article of clothing of claim 1 wherein the at least one connection is selected from a second group of reversible fasteners comprising:
   hook and loop, button snaps, button and buttonhole, magnets, hook and eye, clasps, d-rings, and string-ties.

5. The article of clothing of claim 1 wherein the article of clothing is created in the style selected from the group comprising:
   a t-shirt, a blouse, a sleeveless shirt, a spaghetti strap top, a tube top, a dress, a gown, a brassiere, lingerie, a skirt, a sweater, a long sleeve shirt, a hoodie, a coat, a hospital gown, a tank top, a sports bra, a bandeau, a bathing suit, and pajamas; and
   further wherein, the upper panel and the lower panel at least partially form at least a front of the article of clothing.

6. The article of clothing of claim 1 further comprising:
   at least one reversibly connectable shoulder strap, wherein the shoulder strap comprises a first distal end that has a first connector attached to the upper panel and a second distal end that has a second connector attached to the back panel.

7. The article of clothing of claim 1 wherein the said internal brassiere is irreversibly connected to the article of clothing.

8. The article of clothing of claim 1 wherein the overlapping area is disguised from ready detection by selecting at least one style element selected from the group comprising pleats, patterns, colors, bands, and belts.

* * * * *